(12) United States Patent
Tempco

(10) Patent No.: US 10,864,602 B2
(45) Date of Patent: Dec. 15, 2020

(54) SYSTEM AND METHOD OF MANUFACTURE FOR SPINAL IMPLANT

(71) Applicant: Warsaw Orthopedic, Inc., Warsaw, IN (US)

(72) Inventor: Dale A. Tempco, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 349 days.

(21) Appl. No.: 15/889,355

(22) Filed: Feb. 6, 2018

(65) Prior Publication Data
US 2019/0240782 A1 Aug. 8, 2019

(51) Int. Cl.
| | |
|---|---|
| B23K 26/342 | (2014.01) |
| A61B 17/70 | (2006.01) |
| B23K 26/08 | (2014.01) |
| B23K 26/12 | (2014.01) |
| B33Y 30/00 | (2015.01) |
| B33Y 80/00 | (2015.01) |
| B23K 31/02 | (2006.01) |
| B33Y 10/00 | (2015.01) |
| A61B 17/86 | (2006.01) |
| A61B 17/00 | (2006.01) |

(52) U.S. Cl.
CPC ........ *B23K 26/342* (2015.10); *A61B 17/7001* (2013.01); *A61B 17/866* (2013.01); *B23K 26/0853* (2013.01); *B23K 26/127* (2013.01); *B23K 31/02* (2013.01); *B33Y 10/00* (2014.12); *B33Y 30/00* (2014.12); *B33Y 80/00* (2014.12); *A61B 2017/00526* (2013.01); *B23G 2240/36* (2013.01)

(58) Field of Classification Search
CPC ...... B23K 26/342; B33Y 10/00; B33Y 30/00; A61B 17/8625; A61B 17/866; A61B 17/7001; A61C 19/00; A61C 8/00
USPC ........................................................ 219/76.1
See application file for complete search history.

(56) References Cited

U.S. PATENT DOCUMENTS

| | | | |
|---|---|---|---|
| 5,204,055 A | 4/1993 | Sachs et al. | |
| 8,801,762 B2 | 8/2014 | Willert et al. | |
| 9,511,544 B2 * | 12/2016 | Hemingway | .......... B33Y 50/02 |
| 9,522,019 B2 * | 12/2016 | Biedermann | ...... A61B 17/7031 |
| 10,307,194 B2 * | 6/2019 | Tempco | ................ B29C 64/393 |

(Continued)

FOREIGN PATENT DOCUMENTS

| | | |
|---|---|---|
| KR | 1020100048244 A | 5/2010 |
| WO | 2012166552 A1 | 12/2012 |
| WO | 2017089583 A1 | 6/2017 |

OTHER PUBLICATIONS

International Search Report and Written Opinion for PCT/US2019/016598 the counterpart application dated May 17, 2019, 12 pages.

*Primary Examiner* — Jennifer C Chiang
(74) *Attorney, Agent, or Firm* — Sorell, Lenna & Schmidt, LLP

(57) ABSTRACT

A build plate system includes a body defining at least one cavity. An insert is sized and shaped to fit within the at least one cavity such that the at least one cavity orients the insert for forming at least a portion of a screw shaft thereon by a manufacturing method using an additive manufacturing apparatus. In some embodiments, systems, spinal constructs, surgical instruments and methods are disclosed.

21 Claims, 11 Drawing Sheets

(56) References Cited

U.S. PATENT DOCUMENTS

| | | | |
|---|---|---|---|
| 10,398,559 B2* | 9/2019 | Jones | A61L 27/306 |
| 10,561,456 B2* | 2/2020 | Cawley | A61B 17/866 |
| 2014/0159266 A1 | 6/2014 | Bamberg et al. | |
| 2014/0252685 A1 | 9/2014 | Stucker et al. | |
| 2014/0343706 A1 | 11/2014 | Hart et al. | |
| 2015/0093283 A1* | 4/2015 | Miller | A61F 2/3859 |
| | | | 419/55 |
| 2015/0134063 A1 | 5/2015 | Steinmann et al. | |
| 2015/0209094 A1 | 7/2015 | Anderson | |
| 2016/0157908 A1 | 6/2016 | Cawley et al. | |
| 2016/0184480 A1* | 6/2016 | Cox | B33Y 70/00 |
| | | | 424/423 |
| 2016/0339519 A1 | 11/2016 | Sargent | |
| 2017/0056875 A1 | 3/2017 | Pompa | |
| 2019/0008562 A1* | 1/2019 | Melton | B22F 3/1055 |
| 2019/0375149 A1* | 12/2019 | Limem | B29C 64/112 |

\* cited by examiner

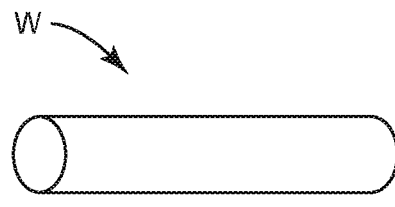
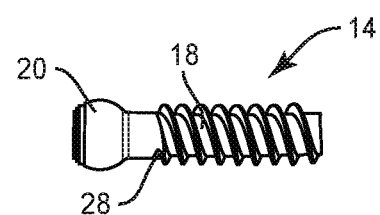
FIG. 4
FIG. 5
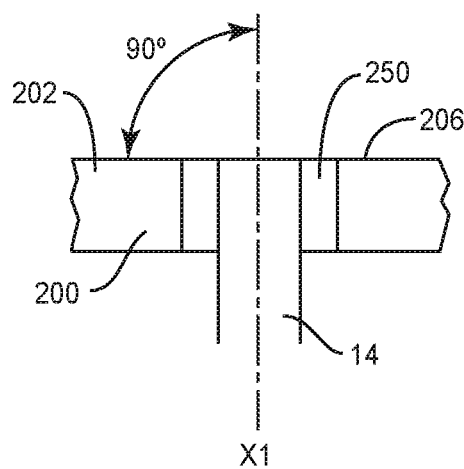
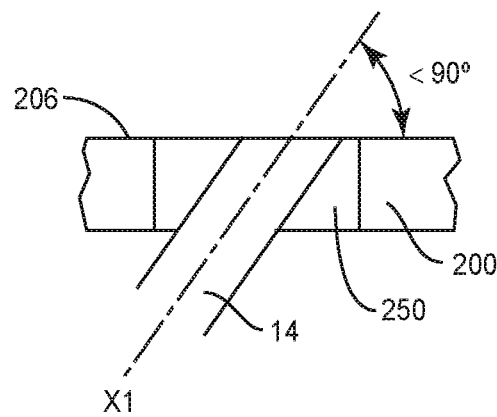
FIG. 6
FIG. 7

SYSTEM AND METHOD OF MANUFACTURE FOR SPINAL IMPLANT

TECHNICAL FIELD

The present disclosure generally relates to medical devices for the treatment of spinal disorders, and more particularly to a spinal implant system having spinal implants manufactured by a method including an additive manufacturing technique.

BACKGROUND

Spinal pathologies and disorders such as scoliosis, kyphosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a build plate system is provided. The build plate system includes a body defining at least one cavity. An insert is sized and shaped to fit within the at least one cavity such that the at least one cavity orients the insert for forming at least a portion of a screw shaft thereon by a manufacturing method using an additive manufacturing apparatus. In some embodiments, systems, spinal constructs, spinal implants, surgical instruments and methods are disclosed.

In one embodiment, a method for fabricating a bone screw is provided. The method comprises the steps of: disposing a build plate within a working chamber of an additive manufacturing apparatus, the plate including at least one cavity; orienting the insert within the at least one cavity such that the at least one cavity orients the insert for forming at least a portion of a screw shaft thereon using the additive manufacturing apparatus based on selected configuration parameters; and forming the at least a portion of the screw shaft by adding material in a layer by layer manner.

In one embodiment, an additive manufacturing apparatus is provided. The additive manufacturing apparatus includes an enclosure defining a working chamber and a laser device. A build plate disposed in the working chamber. The plate defining at least one cavity. An insert sized and shaped to fit within the at least one cavity such that the at least one cavity orients the insert for forming at least a portion of a screw shaft thereon by selective laser melting of a material onto the insert to form the at least a portion of a screw shaft with a powder bed process.

BRIEF DESCRIPTION OF THE DRAWINGS

The present disclosure will become more readily apparent from the specific description accompanied by the following drawings, in which:

FIG. 4 is a perspective view of components of one embodiment of a system in accordance with the principles of the present disclosure;

FIG. 5 is a side view of components of one embodiment of a system in accordance with the principles of the present disclosure;

FIG. 6 is a side view of components of one embodiment of a system in accordance with the principles of the present disclosure;

FIG. 7 is a side view of components of one embodiment of a system in accordance with the principles of the present disclosure;

DETAILED DESCRIPTION

Figure 1:
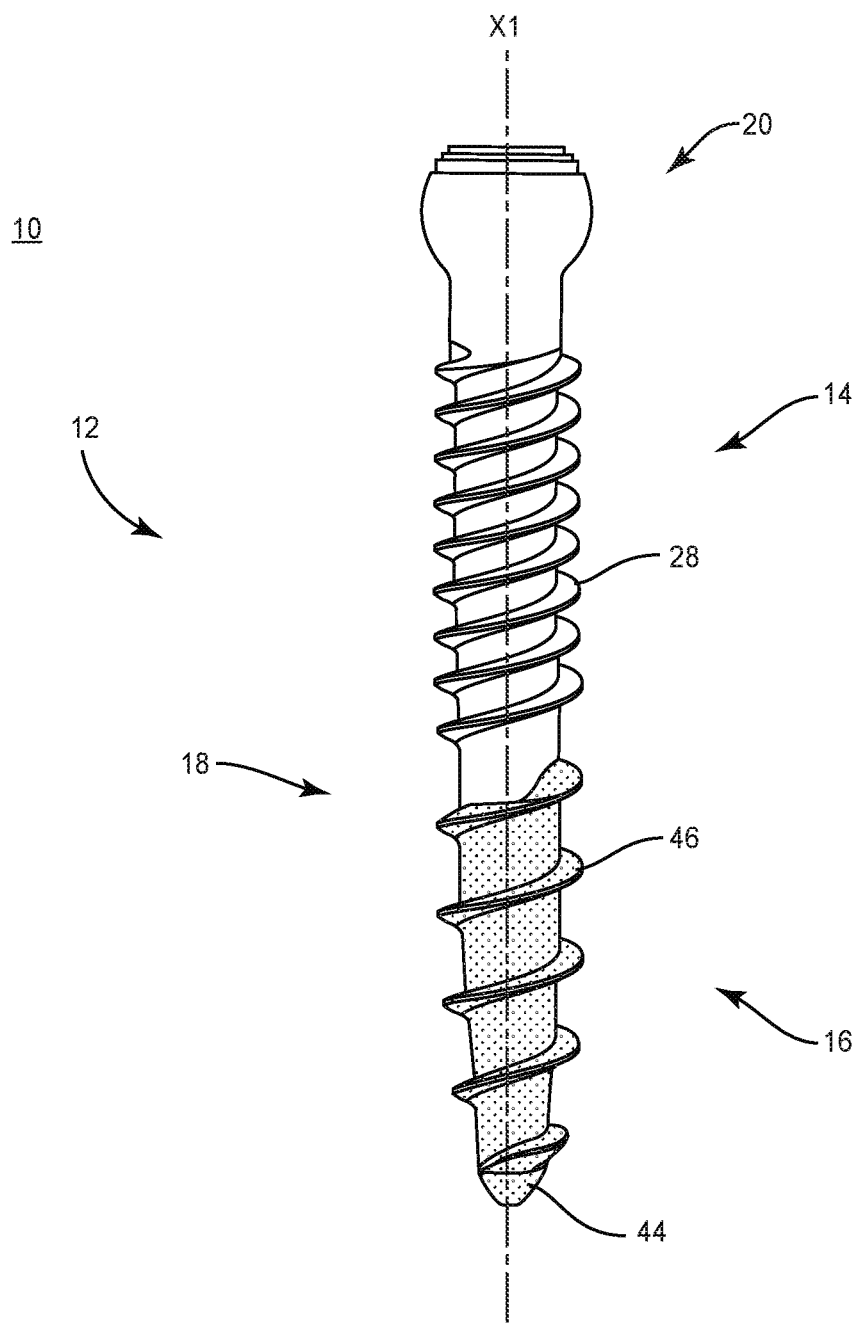
FIG. 1 is a side view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a spinal implant system having spinal implants manufactured by a method including one or more manufacturing techniques. In some embodiments, the spinal implant system includes a spinal implant comprising a bone screw including a hybrid medical device. In some embodiments, the spinal implant includes a bone screw having at least one portion manufactured via an additive manufacturing technique.

In some embodiments, the spinal implant system of the present disclosure comprises a spinal implant, surgical instrument and/or medical device manufactured with a manufacturing system employed with a manufacturing method including one or more additive manufacturing features and materials and/or one or more traditional manufacturing features and materials. In some embodiments, the manufacturing system includes a part, such as, for example, a build plate employed in connection with an additive forming technique. In some embodiments, the build plate includes an additive manufacturing build plate. In some embodiments, the build plate includes inserts. In some embodiments, the inserts are disposable with one or more cavities of the build plate and oriented for forming at least a portion of a spinal implant, surgical instrument and/or medical device thereon by a manufacturing method that includes an additive manufacturing apparatus. In some embodiments, the build plate includes one or more pockets and/or recesses configured for receiving an insert.

In some embodiments, the present manufacturing system includes a modular build plate used in powder fusion bed additive manufacturing. In some embodiments, the build plate is modular such that at least a portion of a spinal implant, surgical instrument and/or medical device are connected to inserts in the build plate. This configuration avoids having to connect the portion of spinal implant, surgical instrument and/or medical device directly to the build plate. In some embodiments, the manufacturing system includes a build plate used in power fusion bed additive manufacturing where the spinal implant, surgical instrument and/or medical device is fused to an insert of the build plate. In some embodiments, this configuration avoids having to remove an entire plate from an additive manufacturing machine. In some embodiments, subsequent to additive manufacturing, the insert is removable from the build plate and the spinal implant, surgical instrument and/or medical device is separated from the insert. In some embodiments, the spinal implant, surgical instrument and/or medical device is connected with the insert, for example, by friction fit, pressure fit, threaded engagement, fusion, bolt connection, clamps, screws and/or dovetail configured mechanisms. In some embodiments, a portion of the spinal implant, surgical instrument and/or medical device is formed and/or manufactured from the insert. In some embodiments, the spinal implant, surgical instrument and/or medical device is removable and/or separated from the insert, for example, by manual disengagement to overcome a friction fit, manual disengagement to overcome a pressure fit, unthreading, fracture, chemical reaction, disengaging a bolt connection, sawing, electrical discharge machining (wire EDM) or other method.

In some embodiments, the present manufacturing system includes an insert that is attachable to a build plate and allows for a spinal implant, surgical instrument and/or medical device to be removed quickly and efficiently from the build plate either independently, in groups and/or in series. In some embodiments, the inserts can be made of various shapes such as round, rectangular or square. In some embodiments, the inserts can be precision ground in a flush configuration with a top surface of a build plate. In some embodiments, the inserts can be attached to a build plate and fixed therewith, for example, via friction fit, pressure fit, threaded engagement, fusion, bolt connection, clamps, screws and/or dovetail configured mechanisms.

In some embodiments, the present manufacturing system increases the efficiency when manufacturing a spinal implant, surgical instrument and/or medical device. In some embodiments, the present manufacturing system increases safety and reduces injury risk to operators as the entire build plate need not be removed from an additive manufacturing machine for removal of a manufactured spinal implant, surgical instrument and/or medical device. In some embodiments, the present manufacturing system reduces and/or eliminates resurfacing costs for build plates. In some embodiments, the inserts can be resurfaced and/or shimmed.

In some embodiments, the spinal implant system of the present disclosure comprises a spinal implant, surgical instrument and/or medical device having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system of the present disclosure comprises a spinal implant, such as, for example, a bone screw manufactured by additive manufacturing methods.

In some embodiments, the bone screw is manufactured by applying additive manufacturing material in areas where the bone screw can benefit from materials and properties of additive manufacturing. In some embodiments, the bone screw is manufactured by additive manufacturing such that a distal portion of the bone screw is manufactured by additive manufacturing while an insert, as described herein, includes a proximal portion of the bone screw. In some embodiments, the proximal portion of the bone screw is manufactured and/or separated from the insert by traditional methods and materials, such as, for example, subtractive manufacturing. In some embodiments, the proximal portion is manufactured by wrought or from other materials that have enhanced physical properties relative to additive materials. In some embodiments, utilizing additive manufacturing to create the distal portion of the bone screw can provide a bone in-growth surface along with complex internal and external features.

In some embodiments, the manufacturing system of the present disclosure comprises additive manufacturing to fabricate a spinal implant, such as, for example, a hybrid bone screw that facilitates bony fixation, ingrowth and purchase with tissue. In some embodiments, the hybrid bone screw provides improvement in stability of the bone screw when the distal portion is engaged with tissue. In some embodiments, the bone screw is disposable with tissue in a cantilever configuration that supports a load on the hybrid bone screw in an even distribution. For example, a proximal portion of a bone screw fabricated from a traditional manufacturing method can include strength and stability features for supporting a load, for example, connection with a spinal rod. A distal portion of the bone screw fabricated from an additive manufacturing method can include fixation, ingrowth and porosity features, for example, to facilitate purchase with tissue. In some embodiments, applications of the present hybrid manufacturing technique employed for producing surgical instruments allows additive features to be added to a surgical instrument such that the surgical instrument includes selected features and/or features with complex internal geometry.

In some embodiments, the proximal portion of the bone screw is manufactured and/or separated from an insert by a manufacturing method that employs a lathe, Swiss lathe, mill turning, whirling, grinding and/or roll forming. In some embodiments, the proximal portion is disposed with an insert, as described herein, in connection with an additive forming technique. In some embodiments, the build plate includes one or a plurality of openings configured for disposal of an insert. In some embodiments, the openings are threaded to facilitate connection of an insert with the build plate. In some embodiments, the threaded surface is utilized to control thread orientation and timing of deposition and/or heating. In some embodiments, the openings are selectively shaped to facilitate connection with the insert. In some embodiments, the build plate includes cavities, such as, for example, pockets that are selectively shaped to facilitate connection with the insert. In some embodiments, a distal face of an insert is engaged with one of the openings such that the distal face is disposed in a flush orientation with a surface of the build plate. In some embodiments, the proximal portion of the bone screw is disposed perpendicular to the build plate. In some embodiments, the proximal portion of the bone screw may be disposed in various orientations relative to the build plate.

In some embodiments, the method of manufacturing the distal portion of the bone screw includes a step of connecting an insert including a proximal portion of the bone screw with the build plate. In some embodiments, the method of manufacturing the distal portion includes the step of providing a heat source to heat a powder deposited on the distal face of the insert including the proximal portion. In some embodiments, the method of manufacturing the distal portion includes the step of leveling the powder to a consistent thickness. In some embodiments, the method of manufacturing the distal portion includes the step of melting the powder. In some embodiments, the method of manufacturing the distal portion includes the step of translating the build plate, such as, for example, in a downward direction to facilitate applying additional layers of the powder. In some embodiments, the method of manufacturing includes the step of disengaging the insert from the build plate and separating the bone screw from the insert.

In some embodiments, the spinal implant system of the present disclosure comprises a threaded pedicle screw including a porous portion for enhancing bony fixation, ingrowth and purchase when implanted in bone. In some embodiments, the porous portion is manufactured on a distal surface of an insert including a proximal portion of the pedicle screw. In some embodiments, the porous portion is formed by 3-D printing. In some embodiments, a distal portion of the pedicle screw may include needle-like protrusions and/or lattice structures, and/or protruding/depressed features, whether regular or irregular. In some embodiments, the materials utilized to manufacture the pedicle screw include stainless steel, titanium, cobalt-chromium, polymers, silicone, biologics and/or tissue. In some embodiments, the pedicle screw can be manufactured using wrought, forged, metal injection molded, roll formed, injection molded and/or machined materials, as described herein. In some embodiments, the distal portion is manufactured by additive manufacturing and connected with the proximal portion. In some embodiments, the distal portion is manufactured by additive manufacturing and mechanically attached with the proximal portion by, for example, welding, threading, adhesives and/or staking.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
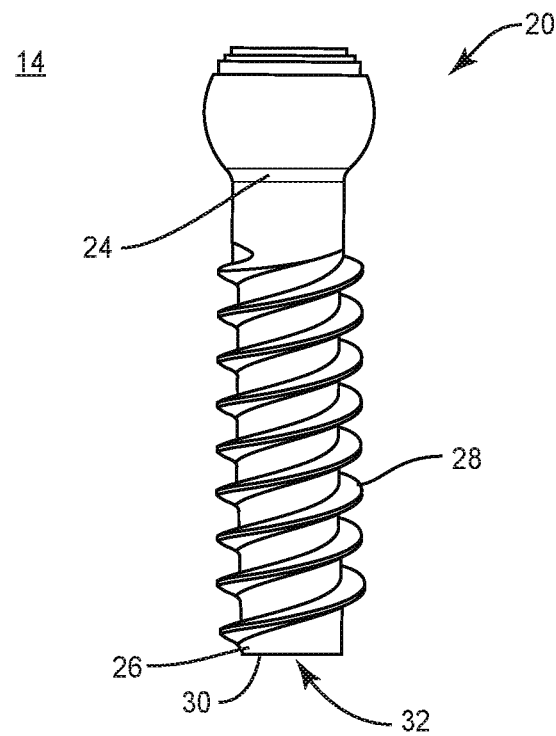
FIG. 2 is a side view of components of the system shown in FIG. 1.
Figure 3:
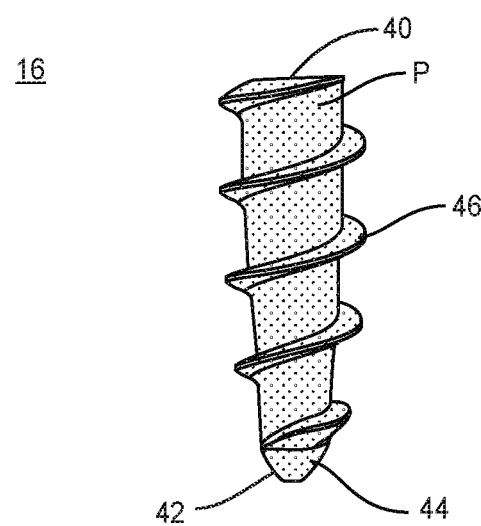
FIG. 3 is a side view of components of the system shown in FIG. 1.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-3, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 9:
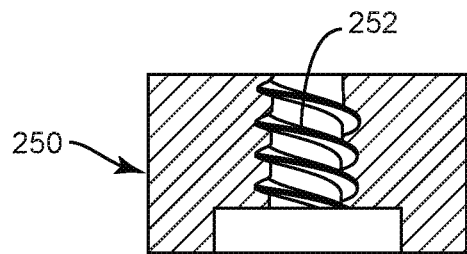
FIG. 9 is a side view of components of one embodiment of a system in accordance with the principles of the present disclosure.

Spinal implant system 10 includes a spinal implant, such as, for example, a bone fastener 12 that defines a longitudinal axis X1. Bone fastener 12 includes an elongated screw shaft 18 having a proximal portion 14 and a distal portion 16 fabricated by an additive manufacturing method, as described herein. In some embodiments, proximal portion 14 is manufactured, as described herein, and connected, for example, via threaded engagement to an insert 250 (FIG. 9) disposable with a build plate 200 (FIG. 12) of an additive manufacturing apparatus (FIG. 13) in connection with a manufacturing method, as described herein. As part of or subsequent to the manufacturing method, insert 250 is removable from build plate 200 and bone fastener 12 is separated from insert 250, as described herein. In some embodiments, insert 250 is disposable with build plate 200 and subsequent to additive manufacturing of distal portion 16, insert 250 is removed from build plate 200 and proximal portion 14 is formed and/or manufactured, via traditional manufacturing methods, as described herein.

In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes portion 14 being formed by a medical machining process. In some embodiments, medical machining processes can include use of computer numerical control (CNC) high speed milling machines, Swiss machining devices, CNC turning with living tooling, wire EDM $4^{th}$ axis and/or Solid Works™ CAD, and Virtual Gibbs™ solid model rendering. In some embodiments, the manufacturing method for fabricating portion 14 and/or portion 16 includes a finishing process, such as, for example, laser marking, tumble blasting, bead blasting, micro blasting and/or powder blasting.

For example, portion 14 is formed by a manufacturing method, which includes feeding a straightened wire W into a machine that cuts wire W at a designated length to form a screw blank, as shown in FIG. 4, and die cuts a head of the screw blank into a selected configuration, as shown in FIG. 5. Portion 14 is manufactured to include a head 20 and a portion of screw shaft 18, as shown in FIG. 2. Portion 14 extends between an end 24 and an end 26. End 24 includes head 20.

Portion 14 includes threads 28, which are fabricated by traditional machining methods, as described herein. Threads 28 extend along all or some of portion 14. Threads 28 are oriented with portion 14 and disposed for engagement with tissue. In some embodiments, threads 28 include a fine, closely-spaced configuration and/or shallow configuration to facilitate and/or enhance engagement with tissue. In some embodiments, threads 28 include a smaller pitch or more thread turns per axial distance to provide a stronger fixation with tissue and/or resist loosening from tissue. In some embodiments, threads 28 include a greater pitch and an increased lead between thread turns. In some embodiments, threads 28 are continuous along portion 14. In some embodiments, threads 28 are continuous along shaft 18 via a selected manufacturing method, as described herein. In some embodiments, threads 28 may be intermittent, staggered, discontinuous and/or may include a single thread turn or a plurality of discrete threads. In some embodiments, other penetrating elements may be located on and/or manufactured with portion 14, such as, for example, a nail configuration, barbs, expanding elements, raised elements, ribs, and/or spikes to facilitate engagement of portion 14 with tissue.

Figure 10:
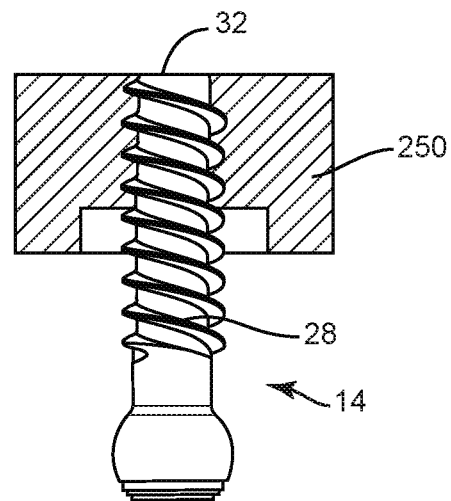
FIG. 10 is a side view of components of one embodiment of a system in accordance with the principles of the present disclosure.
Figure 11:
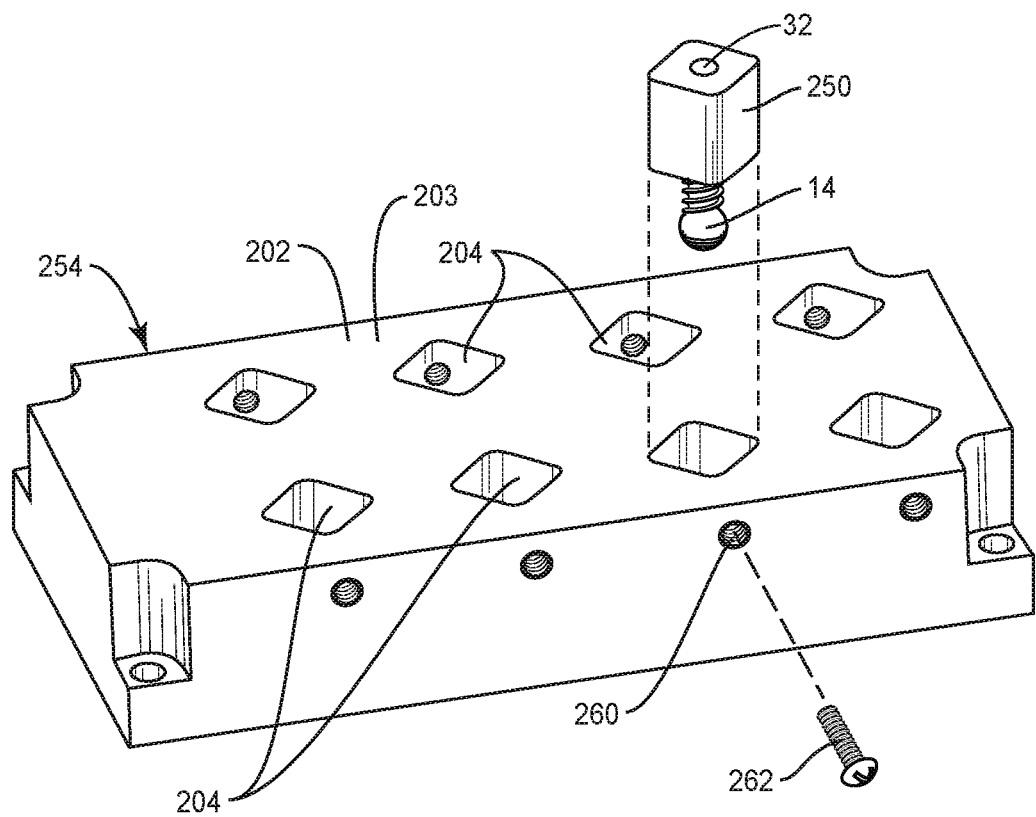
FIG. 11 is a perspective view with parts separated of components of one embodiment of a system in accordance with the principles of the present disclosure.

End 26 includes a surface 30 that defines a distal face 32. In some embodiments, surface 30 may be disposed along a length of portion 14 or at a distalmost surface of portion 14. In some embodiments, portion 14 is threaded with a threaded surface 252 of insert 250 (FIGS. 9 and 10) and insert 250 is mounted with build plate 200 (FIG. 12) such that distal face 32 extends perpendicular to axis X1, as shown in FIG. 6. In some embodiments, distal face 32 may be disposed in various orientations relative to axis X1, such as, for example, transverse and/or at angular orientations, such as acute or obtuse. In one embodiment, as shown in FIG. 7, portion 14 is threaded with a threaded surface 252 of insert 250 and insert 250 is mounted with build plate 200 such that distal face 32 is disposed at an acute angular orientation relative to axis X1.

Figure 12:
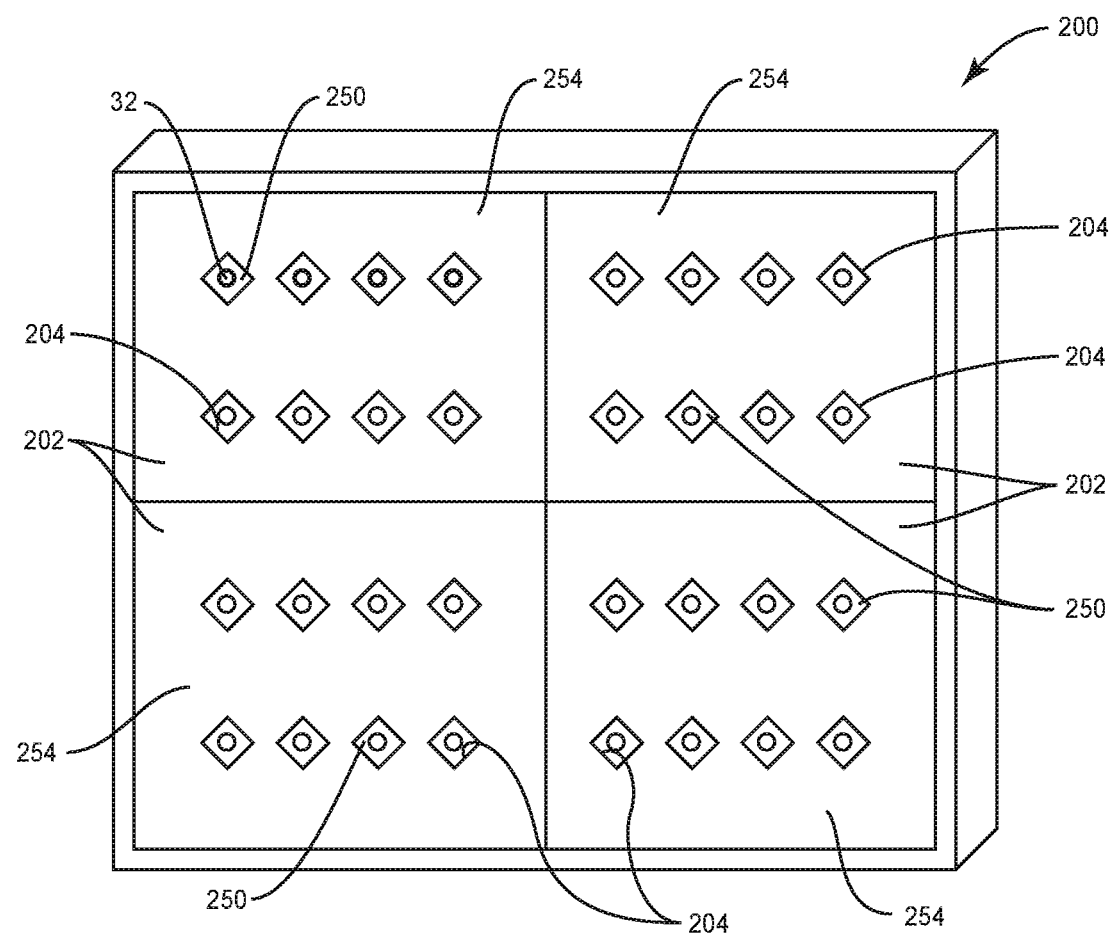
FIG. 12 is a top perspective view of components of one embodiment of a system in accordance with the principles of the present disclosure.
Figure 13:
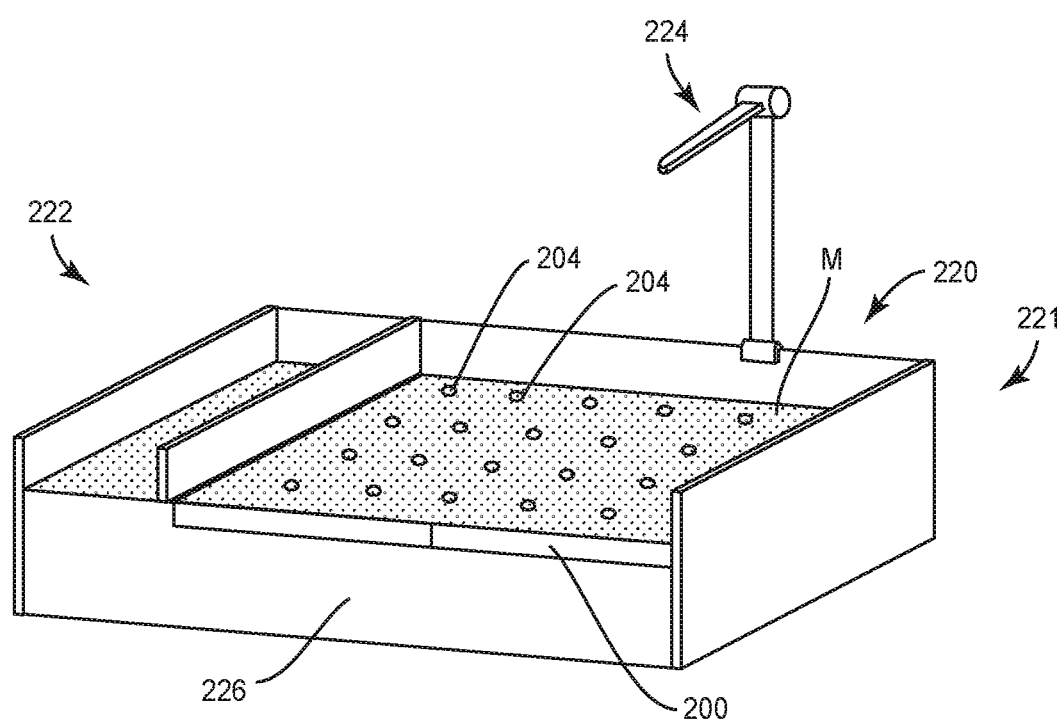
FIG. 13 is a perspective view of components of one embodiment of a system in accordance with the principles of the present disclosure.

With insert 250, including proximal portion 14, fixed with build plate 200, as shown in FIGS. 12 and 13 and described herein, distal face 32 is configured for providing a fabrication platform for forming portion 16 thereon with an additive manufacturing method, as described herein. Distal face 32 has a substantially planar configuration for material deposition and/or heating during an additive manufacturing process for fabricating portion 16 onto distal face 32. In some embodiments, all or only a portion of distal face 32 may have alternate surface configurations, such as, for example, angled, irregular, uniform, non-uniform, offset, staggered, tapered, arcuate, undulating, mesh, porous, semi-porous, dimpled, pointed and/or textured. In some embodiments, distal face 32 may include a nail configuration, barbs, expanding elements, raised elements, ribs, and/or spikes to provide a fabrication platform for forming portion 16 thereon with an additive manufacturing method, as described herein. In some embodiments, all or only a portion of distal face 32 may have alternate cross section configurations, such as, for example, oval, oblong triangular, square, polygonal, irregular, uniform, non-uniform, offset, staggered, and/or tapered.

Portion 16 is fabricated with an additive manufacturing method by disposing a material M (FIG. 14) onto distal face 32, as described herein. Material M is configured and provided, as part of an additive manufacturing method, for fabrication on distal face 32 such that resulting portion 16 is fused with surface 30. In some embodiments, portion 16 is fabricated by depositing material M onto distal face 32 one layer at a time, as described herein.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, portion 16 is manufactured by additive manufacturing, as described herein, and mechanically attached with surface 30 by, for example, welding, threading, adhesives and/or staking.

Figure 8:
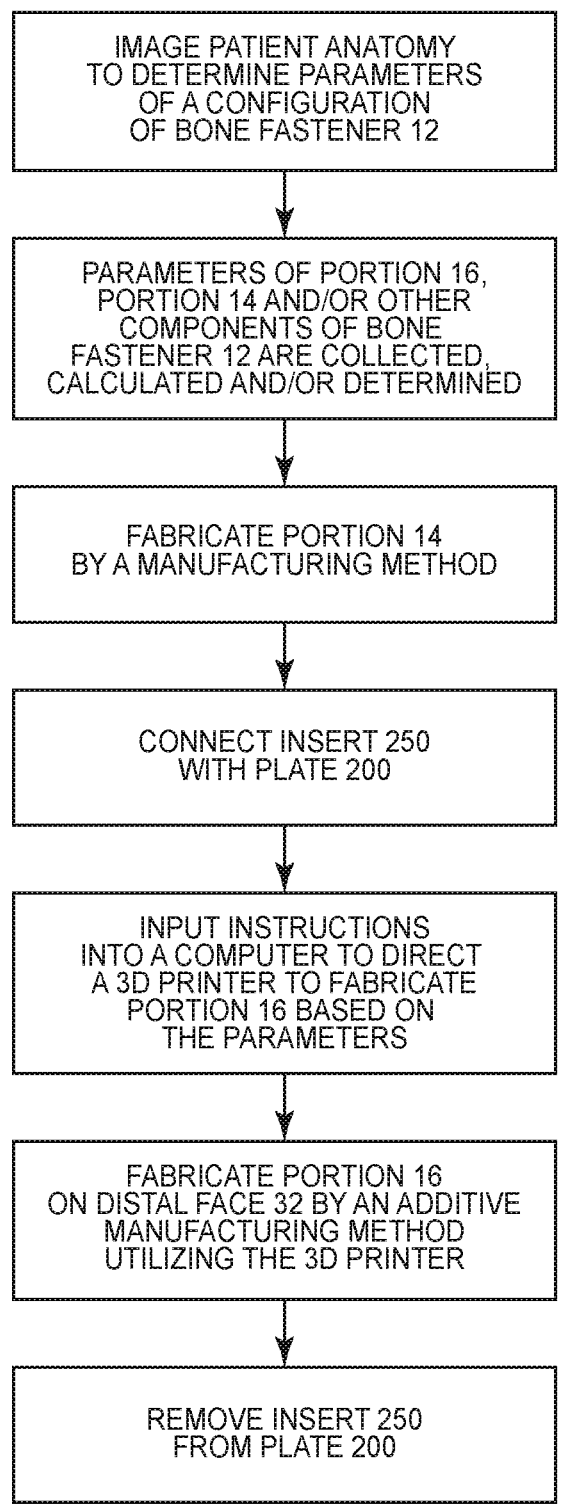
FIG. 8 is a flow diagram illustrating representative steps for producing components of one embodiment of a system in accordance with the principles of the present disclosure.

In one embodiment, as shown in FIG. 8, one or more manufacturing methods for fabricating distal portion 16, proximal portion 14 and/or other components of bone fastener 12 include imaging patient anatomy with imaging techniques, such as, for example, x-ray, fluoroscopy, computed tomography (CT), magnetic resonance imaging (MRI), surgical navigation, and/or acquirable 2-D or 3-D images of patient anatomy. Selected configuration parameters of distal portion 16, proximal portion 14 and/or other components of bone fastener 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of distal portion 16 determined based on patient anatomy and the surgical treatment. In some embodiments, the implant material includes a selected porosity P of distal portion 16, as described herein. In some embodiments, the selected configuration parameters of distal portion 16, proximal portion 14 and/or other components of bone fastener 12 are patient specific. In some embodiments, the selected configuration parameters of distal portion 16, proximal portion 14 and/or other components of bone fastener 12 are based on generic or standard configurations and/or sizes and not patient specific. In some embodiments, the selected configuration parameters of distal portion 16, proximal portion 14 and/or other components of bone fastener 12 are based on one or more configurations and/or sizes of components of a kit of spinal implant system 10 and not patient specific.

For example, based on one or more selected configuration parameters, as described herein, a digital rendering and/or data of a selected distal portion 16, proximal portion 14 and/or other components of bone fastener 12, which can include a 2-D or a 3-D digital model and/or image, is collected, calculated and/or determined, and generated for display from a graphical user interface, as described herein, and/or storage on a database attached to a computer and a processor (not shown), as described herein. In some embodiments, the computer provides the ability to display, via a monitor, as well as save, digitally manipulate, or print a hard copy of the digital rendering and/or data. In some embodiments, a selected distal portion 16, proximal portion 14 and/or other components of bone fastener 12 can be designed virtually in the computer with a CAD/CAM program, which is on a computer display. In some embodiments, the processor may execute codes stored in a computer-readable memory medium to execute one or more instructions of the computer, for example, to transmit instructions to an additive manufacturing device, such as, for example, a 3-D printer. In some embodiments, the database and/or computer-readable medium may include RAM, ROM, EPROM, magnetic, optical, digital, electromagnetic, flash drive and/or semiconductor technology. In some embodiments, the processor can instruct motors or actuators (not shown) that control movement, such as, for example, rotation of spinal implant system 10 components, for example, a build plate 200, insert 250, distal face 32 and/or laser emitting devices, including relative component movement, as described herein.

In some embodiments, the components of spinal implant system 10 can include one or more computer systems. In some embodiments, the components of spinal implant system 10 can include computers and/or servers of a network having a plurality of computers linked to each other over the network, Wi-Fi, Internet, comprise computers connected via a cloud network or in a data drop box. In some embodiments, the graphical user interface may include one or more display devices, for example, CRT, LCD, PDAs, WebTV terminals, set-top boxes, cellular phones, screen phones, smart phones, iPhone, iPad, tablet, wired or wireless communication devices.

Portion 14 is fabricated with threads 28 by a manufacturing method, as described herein. Portion 14 is threaded with threaded surface 252 of insert 250 and the assembly of insert 250 with portion 14 is connected with a section 254 of build plate 200, as shown in FIGS. 9-13, in connection with an additive forming process and a manufacturing method for fabricating distal portion 16. In some embodiments, portion 14 is connected with insert 250, for example, by friction fit, pressure fit, threaded engagement, fusion, bolt connection, clamps, screws and/or dovetail configured mechanisms.

Section 254 includes a body 202 that defines one or a plurality of openings, such as, for example, pockets 204. Pockets 204 are in various embodiments disposed in rows and spaced apart along body 202. Each pocket 204 extends a depth within body 202 and is configured for receiving insert 250, including proximal portion 14, to orient distal face 32 as a fabrication platform for forming portion 16 thereon, such as, for example, with an additive manufacturing method, as described herein. Distal face 32 is disposed with pocket 204 in a flush alignment with a surface 203 of body 202 to orient distal face 32 for manufacturing. The manufacturing process in various embodiments uses apparatus 222 (FIG. 13) and includes adding material M as a powder bed covering distal face 32 and body 202, and laser melting material M at distal face 32.

Section 254 includes a plurality of threaded side openings 260 configured for disposal of a threaded screw 262, in various embodiments. Upon disposal of insert 250 including portion 14 with pocket 204, screw 262 is threaded with opening 260 to engage insert 250 to fix insert 250 with section 254. In some embodiments, inserts 250 can be attached to section 254 and fixed therewith, for example, via friction fit, pressure fit, threaded engagement, fusion, bolt connection, clamps, screws and/or dovetail configured mechanisms.

Build plate 200 includes one or a plurality of sections 254 that are relatively disposed in a selected configuration, as shown in FIG. 12. For example, build plate 200 includes four sections 254 disposed in an adjacent and side by side relation. Inserts 250 are selectively oriented and configured with sections 254 of build plate 200 for fabricating selectively configured distal portions 16, as described herein, and disposed with a working chamber 220 of a powder bed additive manufacturing apparatus 222, as shown in FIG. 13. A plurality of inserts 250 are mounted with build plate 200 to manufacture a plurality of bone fasteners 12, as described herein. Insert 250 is configured such that distal face 32 is disposed in flush alignment with surface 203 of body 202 of build plate 200. An enclosure 221 of apparatus 222 defines working chamber 220.

Apparatus 222 includes a heating device, such as, for example, a laser device 224 disposed with working chamber 220 that fuses material M, which includes a powder, as described herein, in a slice by slice, layer by layer formation of portion 16 onto distal face 32. In some embodiments, laser device 224 includes an interactive laser and optics system that produces a laser beam scanned over a layer of material M powder disposed on build plate 200 (FIGS. 13 and 15) to selectively heat the powder according to instructions received from the computer and processor based on the digital rendering and/or data of the selected configuration of portion 16. Laser device 224 heats a thin layer of material M powder in accordance with slice data based on the digital rendering and/or data to fabricate portion 16, layer by layer, via an additive manufacturing technique. See, for example, the additive and three dimensional manufacturing systems and methods described in U.S. Pat. No. 5,204,055 and US Patent Application Publication No. 2014/0252685, the contents of each of these references being hereby incorporated by reference herein in their respective entireties.

Figure 16:
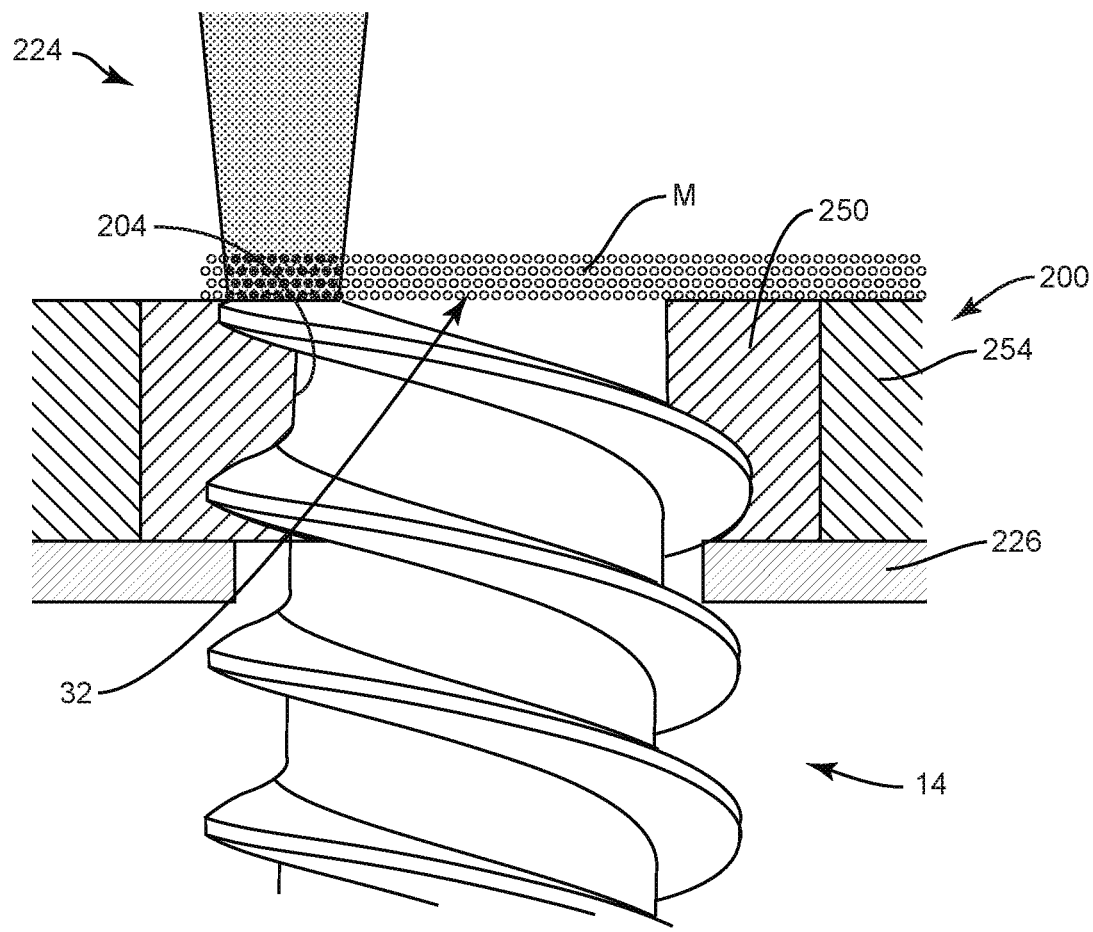
FIG. 16 is a side, in part cross section view of components of one embodiment of a system in accordance with the principles of the present disclosure.

In some embodiments, apparatus 222 includes a radiation source that melts and solidifies material M disposed with distal face 32 into a desired three-dimensional shape based on the selected configuration parameters, as described herein. In some embodiments, the radiation source includes laser device 224, which comprises a carbon dioxide laser. In some embodiments, laser device 224 may include a beam of any wavelength of visible light or UV light. In some embodiments, apparatus 222 emits alternative forms of radiation, such as, for example, microwave, ultrasound or radio frequency radiation. In some embodiments, laser device 224 is configured to be focused on a portion of distal face 32 to sinter material M deposited thereon, as shown in FIG. 16. In some embodiments, laser device 224 emits a beam having a diameter between about 0.01 mm and about 0.8 mm. In some embodiments, the diameter of the beam may be between about 0.1 mm and about 0.4 mm. In some embodiments, the diameter of the beam is adjustable to customize the intensity of the sintering.

In some embodiments, pockets 204 are oriented with plate 200 to selectively orient insert 250 including portion 14, in connection with the commands and instructions provided by apparatus 222, as described herein, for controlling thread orientation and timing of deposition and/or heating of material M with distal face 32 to fabricate portion 16 in accordance with selected configuration parameters, as described herein. For example, distal face 32 is disposed with pocket 204 in a perpendicular orientation relative to surface 203 and axis X1, as shown in FIG. 6. In some embodiments, distal face 32 may be disposed with pocket 204 in various orientations relative to surface 203, such as, for example, transverse and/or at angular orientations, such as acute or obtuse. In one embodiment, as shown in FIG. 7, surface 254 is threaded with body 202 and distal face 32 is disposed with pocket 204 at an acute angular orientation relative to axis X1. In some embodiments, portion 14 may be disposed with pocket 204 in alternate connection configurations, such as, for example, friction fit, pressure fit, locking protrusion/recess, locking keyway and/or adhesive.

In some embodiments, plate 200 may be substantially non-conductive. In some embodiments, plate 200 may be ceramic, glass or non-metallic. In some embodiments, plate 200 may be formed of an electrical insulating material that is operable to prevent an external heat control mechanism from heating plate 200 to a sintering temperature of material M that is utilized to form the layers.

Figure 14:
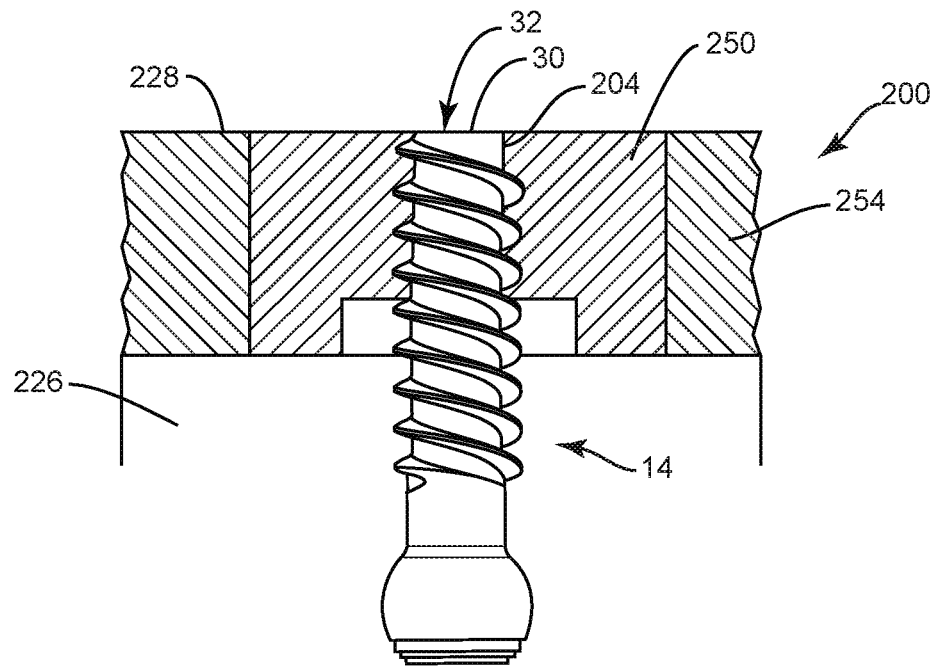
FIG. 14 is a side view, in part cross section, of components of one embodiment of a system in accordance with the principles of the present disclosure.

Inserts 250 including portion 14 are mounted with sections 254 for assembly with build plate 200, as described herein, and build plate 200 is mounted with a platform 226 of apparatus 222 such that inserts 250 and/or build plate 200 can be moved relative to enclosure 221 in one or more directions to generate distal portion 16 onto distal face 32, layer by layer, based on the digital rendering and/or data, as shown in FIG. 14. In some embodiments, one or more inserts 250 and/or build plate 200 can be translated vertically, horizontally or diagonally, rotated, pivoted, raised and/or lowered to generate distal portion 16. In some embodiments, build plate 200 can be moved relative to enclosure 221 slidably, continuously, incrementally, intermittently, automatically, manually, selectively and/or via computer/processor control. In some embodiments, apparatus 222 comprises an additive manufacturing device that employs selective laser melting with a powder bed process to create 3D objects. See, for example, the Lasertec 30 SLM additive manufacturing machine manufactured by DMG MORI Co. Ltd. located at 2-35-16 Meieki, Nakamura-ku, Nagoya City 450-0002, Japan.

In some embodiments, apparatus 222 is connected with one or more computer systems, processors and databases, as described herein, to receive commands and instructions for creating distal portion 16 onto distal face 32 by selective laser melting with a powder bed process. For example, the commands and instructions are based on the one or more selected configuration parameters of a selected distal portion 16 generated for display from a graphical user interface and/or stored on a database, as described herein. In some embodiments, apparatus 222 and/or the one or more computer systems can include a keyboard (not shown) to receive commands and instructions from a user. In some embodiments, inputs may also be received from another computer or any suitable computer user interface. In some embodiments, the processor receives the instructions and directs apparatus 222 to fabricate portion 16 based on the received instructions.

Figure 15:
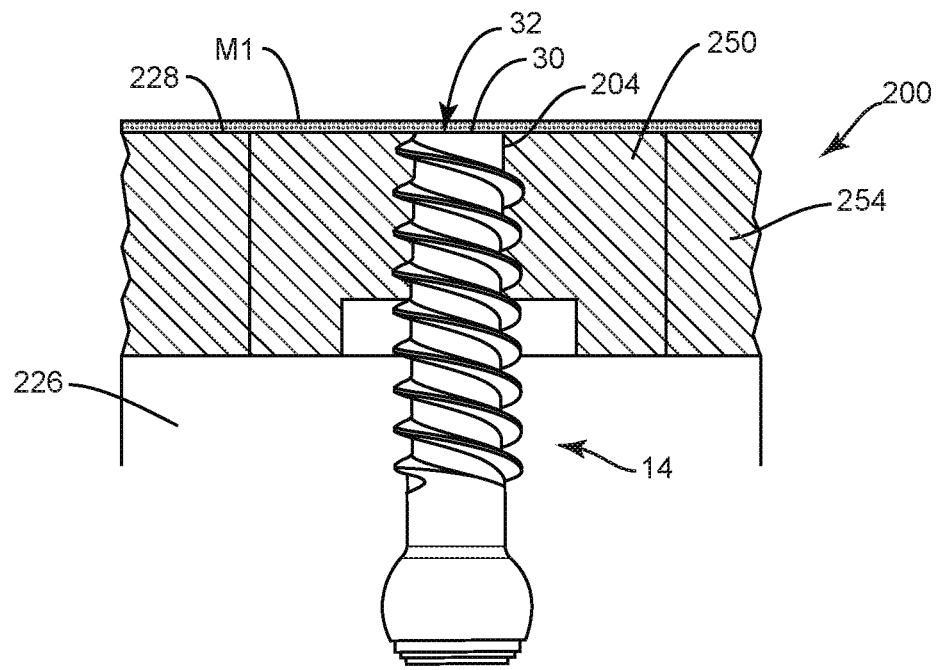
FIG. 15 is a side view, in part cross section, of components of one embodiment of a system in accordance with the principles of the present disclosure.

Material M powder is in various embodiments introduced in working chamber 220, as shown in FIGS. 15 and 16. Apparatus 222 includes a coating arm (not shown) that translates within working chamber 220 to deposit layers of material M powder along a planar surface 228 of plate 200. In some embodiments, the coating arm includes a blade that executes a displacement motion to sweep and/or deposit material M powder across distal face 32 and surface 228. In some embodiments, material M is introduced over the entire cross section of working chamber 220. Material M in various embodiments is leveled by the blade to a uniform and/or consistent thickness according to the selected configuration parameters, as described herein. In some embodiments, a powder bed is formed around portion 16 by excess powder accumulated during manufacture of each layer of portion 16. In some embodiments, the powder bed is configured as a support material during fabrication of portion 16 as the part being constructed is surrounded by un-sintered powder at all times. In some embodiments, material M may include, such as, for example, stainless steel, titanium, cobalt-chromium, polymers, silicone, biologics and/or tissue. In some embodiments, a layer volume of material M powder is about 300×300×300 mm$^3$. In some embodiments, a cartridge-type supply/collection system for material M is provided to facilitate powder delivery and recycling.

With reference to FIGS. 15 and 16, laser device 224 focuses a laser beam to a layer M1 of material M powder disposed with surface 228. Laser device 224 heats, melts and/or softens layer M1 to selectively heat material M powder according to instructions received from the computer and processor based on the digital rendering and/or data of the selected configuration to produce a layer of portion 16. Laser device 224 articulates relative to plate 200 such that the supplied beam is focused on the selected portions of material M deposited on distal face 32. The beam is focused onto portions of material M on distal face 32 to melt or sinter material M into a desired shape based on the selected configuration parameters.

Platform 226 moves plate 200 and/or inserts 250 including portion 14 relative to enclosure 221. In some embodiments, motors, actuators and/or gear mechanisms (not shown) are connected with platform 226 and plate 200 to control movement of plate 200 and/or inserts 250 relative to enclosure 221, as described herein, for example, vertically downward to translate portion 16 during fabrication of the successive layers of portion 16 according to instructions received from the computer and processor.

Figure 17:
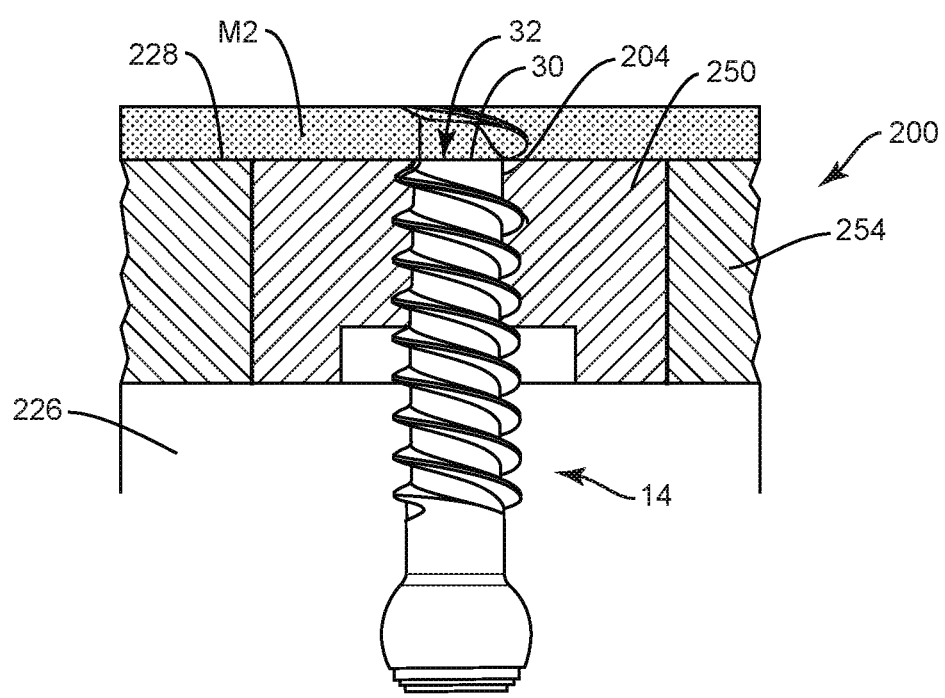
FIG. 17 is a side, in part cross section view of components of one embodiment of a system in accordance with the principles of the present disclosure.

After one layer of portion 16 is melted, plate 200 and/or insert 250 including portion 14, and the fabricated layer of portion 16 is translated vertically downward such that the blade moves across surface 228 to sweep and/or deposit another layer M2 of material M powder across the prior fabricated layer on distal face 32 and plate 200 for melting, as shown in FIG. 17. Layer M2 is leveled by the blade to a thickness according to the selected configuration parameters, as described herein. Laser device 224 heats, melts and/or softens layer M2 to selectively heat material M powder to produce a successive layer of portion 16 according to instructions received from the computer and processor.

Figure 18:
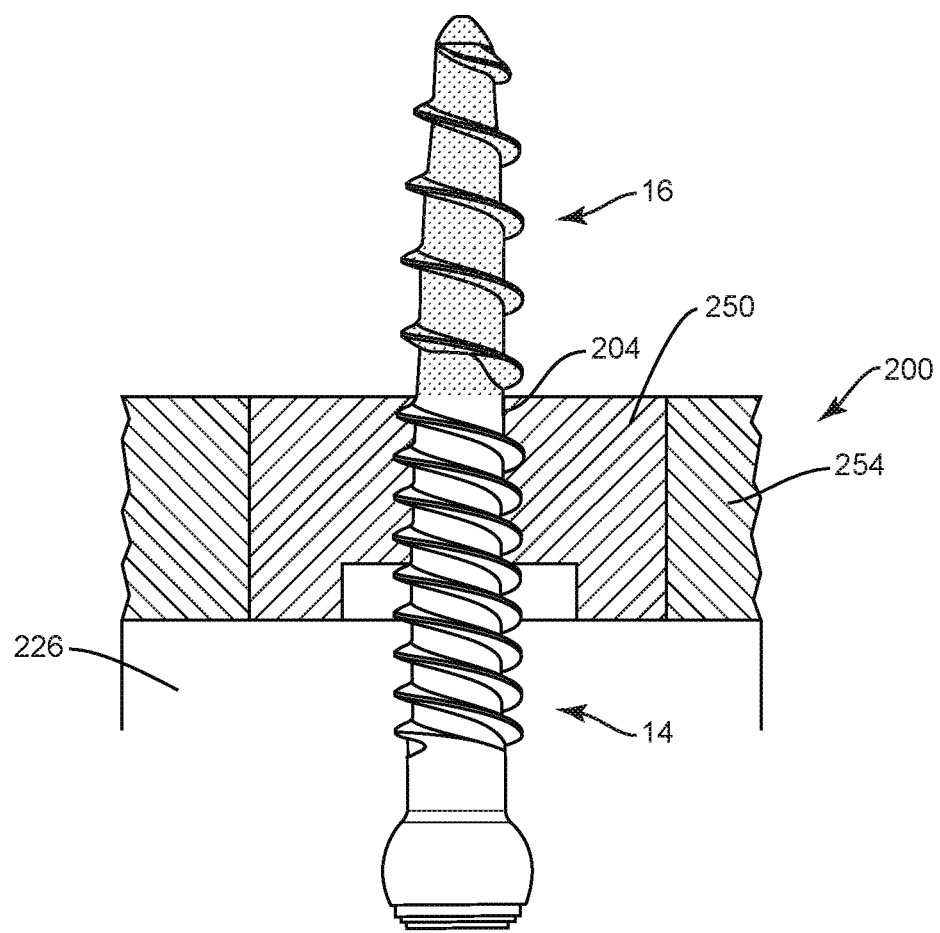
FIG. 18 is a side, in part cross section view of components of one embodiment of a system in accordance with the principles of the present disclosure.

Portion 16 is built up layer by layer and the melting process is repeated slice by slice, layer by layer, until the final layer of material M is melted and portion 16 is complete, as shown in FIG. 18. Portion 16 is formed on distal face 32 to extend between an end 40 and end 42 (FIG. 3) according to instructions received from the computer and processor, and end 40 is fused with surface 30. End 42 includes a distal tip 44. In some embodiments, material M is subjected to direct metal laser sintering (DMLS®), selective laser sintering (SLS), fused deposition modeling (FDM), or fused filament fabrication (FFF), or stereolithography (SLA).

Portion 16 is fabricated according to instructions received from the computer and processor based on the digital rendering and/or data of the selected configuration, via the additive manufacturing process described herein to include a thread 46 that extends between end 40 and distal tip 44. Thread 46 is formed layer by layer by fabrication of portion 16, as described herein. Thread 46 is fabricated to extend along all or some of portion 16. In some embodiments, thread 46 is fabricated to include a fine, closely-spaced and/or shallow configuration to facilitate and/or enhance engagement with tissue. In some embodiments, thread 46 is fabricated to include a greater pitch and an increased lead between thread turns than thread 28, as shown in FIG. 1. In some embodiments, thread 46 is fabricated to include a smaller pitch or more thread turns per axial distance than thread 28 to provide a stronger fixation with tissue and/or resist loosening from tissue. In some embodiments, thread 46 is fabricated to be continuous along portion 16. In some embodiments, thread 46 is fabricated to be intermittent, staggered, discontinuous and/or may include a single thread turn or a plurality of discrete threads. In some embodiments, portion 16 is fabricated to include penetrating elements, such as, for example, a nail configuration, barbs, expanding elements, raised elements, ribs, and/or spikes. In some embodiments, thread 46 is fabricated to be self-tapping or intermittent at distal tip 44. In some embodiments, distal tip 44 may be rounded. In some embodiments, distal tip 44 may be self-drilling.

Each insert 250, individually, in series or in groups, is disengaged from the respective sections 254 of plate 200 upon fabrication of portion 16 via an additive manufacturing method, as described herein. For example, screws 262 are unthreaded from openings 260 and inserts 250 are removed from pockets 204. Portion 14 is separated and removed from insert 250 to provide bone fastener 12 by unthreading and/or a manufacturing process such as wire EDM and/or a traditional manufacturing method, as described herein. In some embodiments, portion 14 is separated and removed from insert 250 by, for example, manual disengagement to overcome a friction fit, manual disengagement to overcome a pressure fit, fracture, chemical reaction and/or sawing. In some embodiments, insert 250 is removed from build plate 200 and proximal portion 14 is formed and/or manufactured via traditional methods, as described herein, from insert 250. In some embodiments, portion 14 and/or portion 16 is subjected to a finishing process, such as, for example, laser marking, tumble blasting, bead blasting, micro blasting and/or powder blasting. In some embodiments, the additive manufacturing method may include a 3-D printing head. In some embodiments, the additive manufacturing method may include a temperature control unit such as, for example, a heating or cooling unit to control a temperature of distal face 32. In some embodiments, the computer and processor provide instructions for coordination of simultaneous and/or ordered movement of plate 200, insert 250, distal face 32, laser device 224, components of apparatus 222 and/or introduction and layering of material M powder.

In some embodiments, portion 16 is fabricated in a configuration having a porosity P via the additive manufacturing method, as described herein. In some embodiments, portion 16 is fabricated having a porosity P with a porogen that is spheroidal, cuboidal, rectangular, elongated, tubular, fibrous, disc-shaped, platelet-shaped, polygonal or a mixture thereof. In some embodiments, a porosity of portion 16 is based on a plurality of macropores, micropores, nanopores structures and/or a combination thereof.

In some embodiments, the porogen is configured to diffuse, dissolve, and/or degrade after implantation into portion 16 leaving a pore. The porogen may be a gas (e.g., carbon dioxide, nitrogen, argon or air), liquid (e.g., water, blood lymph, plasma, serum or marrow), or solid (e.g., crystalline salt, sugar). The porogen may be a water-soluble chemical compound such as a carbohydrate (e.g., polydextrose, dextran), salt, polymer (e.g., polyvinyl pyrrolidone), protein (e.g., gelatin), pharmaceutical agent (e.g., antibiotics), or a small molecule. In other aspects, the porous implant includes as a porogen polysaccharides comprising cellulose, starch, amylose, dextran, poly(dextrose), glycogen, poly(vinylpyrollidone), pullulan, poly(glycolide), poly(lactide), and/or poly(lactide-co-glycolide). In other aspects, the useful porogens include without limitations hydroxyapatite or polyethylene oxide, polylactic acid, polycaprolactone. Peptides, proteins of fifty amino acids or less or a parathyroid hormone are also useful porogens.

In some embodiments, the porous configuration of portion 16 can exhibit high degrees of porosity over a wide range of effective pore sizes. In some embodiments, the porous configuration of portion 16 may have, at once, macroporosity, mesoporosity, microporosity and nanoporosity. Macroporosity is characterized by pore diameters greater than about 100 microns. Mesoporosity is characterized by pore diameters between about 100 microns about 10 microns; and microporosity occurs when pores have diameters below about 10 microns. Microporous implants have pores of diameters below 9 microns, 8 microns, 7 microns, 6 microns, 5 microns, 4 microns, 3 microns, 2 microns, and 1 micron. Nanoporosity of nanopores is characterized by pore diameters of about 1 nm and below.

In some embodiments, portion 16 is fabricated with a material having a porosity P that is created by an additive manufacturing method, as described herein, of a polymer material, for example, a polymer, onto a bed of particles which are not soluble in the polymer and which can be subsequently leached by a non-solvent for the polymer. In this case, the polymer which forms portion 16 is printed onto a bed of particles such as salt, sugar, or polyethylene oxide. After the additive manufacturing method is complete, portion 16 is removed from the powder bed and placed in a non-solvent for the implant material which will dissolve the particles. For example, polylactic acid in chloroform could be 3-D printed onto a bed of sugar particles, and the sugar can subsequently be leached with water.

In some embodiments, portion 16 is fabricated with a material having a porosity P that is created by an additive manufacturing method, as described herein, by printing a solution containing an implant material onto a heated bed of polymer. An example is 3-D printing polylactic acid in chloroform onto a bed of PLA particles heated to 100° C. The boiling point of chloroform is 60° C., and it will thus boil on hitting the particle bed, causing a foam to form. This method of creating porosity is similar to 3-D printing a solution containing the implant material onto a bed containing a foaming agent, which is another way of achieving porosity.

In some embodiments, bone fastener 12 includes an implant receiver (not shown) connectable with head 20. In some embodiments, bone fastener 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw. In some embodiments, the implant receiver can be attached by manual engagement and/or non-instrumented assembly, which may include a practitioner, surgeon and/or medical staff grasping the implant receiver and shaft 18 and forcibly snap or pop fitting the components together. In some embodiments, spinal implant system 10 comprises a kit including a plurality of bone fasteners 12 of varying configuration, as described herein. In some embodiments, bone fastener 12 is selected from the kit and employed with a treatment at the surgical site.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A build plate system comprising:
   a body comprising a surface defining at least one cavity, and
   an insert sized and shaped to fit within the at least one cavity such that the at least one cavity orients the insert for forming at least a portion of a screw shaft thereon by a manufacturing method using an additive manufacturing apparatus,
   wherein the at least one cavity is selectively oriented to control distal portion thread formation, material deposition timing and/or material heating.

2. A build plate as recited in claim 1, wherein the insert is separate from and attachable with the surface.

3. A build plate as recited in claim 1, wherein the insert is removable from the surface.

4. A build plate as recited in claim 1, wherein the cavity includes a pocket extending a depth within the body.

5. A build plate as recited in claim 1, wherein the cavity includes a plurality of spaced apart pockets.

6. A build plate as recited in claim 1, wherein the cavity includes a plurality of pockets oriented in rows along the surface.

7. A build plate as recited in claim 1, wherein the surface includes a plurality of connected sections.

8. A build plate as recited in claim 1, wherein the surface includes a planar surface configured as a powder bed of the additive manufacturing apparatus.

9. A build plate as recited in claim 1, wherein the additive manufacturing apparatus includes an enclosure defining a working chamber configured to receive the body.

10. A build plate as recited in claim 9, wherein the surface is movable in a plurality of directions relative to the enclosure.

11. A build plate as recited in claim 9, wherein the additive manufacturing apparatus includes a processor that, in operation of the apparatus, controls movement of the surface relative to the enclosure.

12. A build plate as recited in claim 1, wherein the insert includes a distal face disposed, in performance of the manufacturing method, in a flush orientation with a planar surface of the surface.

13. A build plate as recited in claim 1, wherein the insert includes a distal face having a planar configuration.

14. A build plate as recited in claim 1, wherein the insert includes a distal face having an angled configuration.

15. A build plate system comprising:
a body comprising a surface defining at least one cavity, and
an insert sized and shaped to fit within the at least one cavity such that the at least one cavity orients the insert for forming at least a portion of a screw shaft thereon by a manufacturing method using an additive manufacturing apparatus,
wherein the cavity includes a plurality of pockets oriented in rows along the surface.

16. A build plate as recited in claim 15, wherein the insert is separate from and attachable with the surface.

17. A build plate as recited in claim 15, wherein the insert is removable from the surface.

18. A build plate system comprising:
a body comprising a surface defining at least one cavity, and
an insert sized and shaped to fit within the at least one cavity such that the at least one cavity orients the insert for forming at least a portion of a screw shaft thereon by a manufacturing method using an additive manufacturing apparatus,
the surface includes a plurality of connected sections.

19. A build plate as recited in claim 18, wherein the insert is separate from and attachable with the surface.

20. A build plate as recited in claim 18, wherein the insert is removable from the surface.

21. A build plate system comprising:
a body defining at least one cavity, and
an insert sized and shaped to fit within the at least one cavity such that the at least one cavity orients the insert for forming at least a portion of a screw shaft thereon by a manufacturing method using an additive manufacturing apparatus,
wherein the insert includes a distal face having an angled configuration.

* * * * *